United States Patent
Verness et al.

(10) Patent No.: US 6,285,910 B1
(45) Date of Patent: Sep. 4, 2001

(54) MEDICAL ELECTRICAL LEAD

(75) Inventors: David D. Verness, Forest Lake; George M. Huepenbecker, Vadnais Heights; Dale A. Wahlstrom, Plymouth, all of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 08/843,763

(22) Filed: Apr. 21, 1997

(51) Int. Cl.[7] ............................................. A61N 1/04
(52) U.S. Cl. ............................................. 607/122
(58) Field of Search ............................ 607/116, 119, 607/122, 132

(56) References Cited

U.S. PATENT DOCUMENTS

| | | | |
|---|---|---|---|
| 3,474,791 | * 10/1969 | Bentov | 607/132 |
| 3,572,344 | 3/1971 | Bolduc . | |
| 3,844,292 | 10/1974 | Bolduc . | |
| 4,033,355 | 7/1977 | Amundson . | |
| 4,559,951 | * 12/1985 | Dahl et al. | 607/122 |
| 5,231,996 | 8/1993 | Bardy et al. . | |
| 5,545,203 | 8/1996 | Doan . | |
| 5,591,142 | 1/1997 | Van Erp . | |

FOREIGN PATENT DOCUMENTS

| | | | |
|---|---|---|---|
| 3 640 033 | * | 5/1988 | (DE) . |
| 0 574 358 | * | 12/1993 | (EP) . |
| 0 672 431 | * | 9/1995 | (EP) . |
| 0 672 432 | * | 9/1995 | (EP) . |

OTHER PUBLICATIONS

U.S. Patent Application SN 08/843,765, filed Apr. 21, 1997, "Fracture Resistant Medical Electrical Lead".

* cited by examiner

*Primary Examiner*—William E. Kamm (57) ABSTRACT

An implantable lead which has an increased resistance to fracture and has the capability of continued function after fracture of a conductor. The lead is provided with a coiled conductor which may be monofilar or multifilar and which extends along the length of the lead, running from an electrical connector at the proximal end of the lead to an electrode at or near the distal end of the lead. In addition, the lead is provided with a stranded conductor which is electrically coupled to the coiled conductor at point along the lead body located proximal to the point of expected breakage of the coiled conductor and at a point along the lead body located distal to the point of expected breakage. The proximal and distal ends of the stranded conductor in some embodiments are also mechanically coupled to the coiled conductor.

35 Claims, 10 Drawing Sheets

MEDICAL ELECTRICAL LEAD

BACKGROUND OF THE INVENTION

The present invention relates to implantable electrical leads generally, and more specifically to cardiac pacing leads.

The conductors in cardiac pacing leads occasionally have a tendency to fracture due to repetitive application of stress to the conductor. One way in which this problem has previously been addressed is by reinforcing the lead body in the area in which stress is to be expected, as in U.S. Pat. No. 5,545,203, issued to Doan et al. This patent is directed primarily toward reinforcing the lead against fracture due to application of compressive forces. Reinforcement of the lead body is also disclosed in U.S. Pat. No. 5,591,142, issued to Van Erp et al. It has also been proposed to reinforce the lead body by means of adding a tensile reinforcement as in U.S. Pat. No. 5,231,996 issued to Bardy et al. In this patent, the lead is provided with a non-conductive tensile member such as a polyester cord, which runs the length of the lead body. Other leads having cords or reinforcements running throughout their length are disclosed in U.S. Pat. No. 3,844,292 and U.S. Pat. No. 3,572,344 issued to Bolduc. A third proposal for dealing with the possibility of conductor fracture is to render the portion of the lead body in direct contact with the conductor conductive by addition of carbon or other conductive material, as disclosed in U.S. Pat. No. 4,033,355, issued to Ammundson.

SUMMARY OF THE INVENTION

The present invention is directed toward providing a lead which has an increased resistance to fracture and has the capability of continued function after fracture of a conductor. The lead is provided with a coiled conductor which may be monofilar or multifilar and which extends along the length of the lead, running from an electrical connector at the proximal end of the lead to an electrode at or near the distal end of the lead. In addition, the lead is provided with a stranded conductor which extends along the coiled conductor from a point along the lead body located proximal to the point of expected breakage of the coiled conductor to a point along the lead body located distal to the point of expected breakage. The proximal and distal ends of the stranded conductor in some embodiments are electrically and mechanically coupled to the coiled conductor, limiting the extensibility of the coiled conductor, rendering the coiled conductor less susceptible to axially applied tensile forces and also providing for continued electrical connection to the electrode, in the event that the coiled conductor fractures intermediate the proximal and distal ends of the stranded conductor. In alternative embodiments, the stranded conductor may be coupled only at its proximal or distal end to the coiled conductor or may simply be located in the same lumen of the lead as the coiled conductor, without mechanical connection to the coiled conductor.

DETAILED DESCRIPTION OF THE PREFERRED EMBODIMENTS

Figure 1:
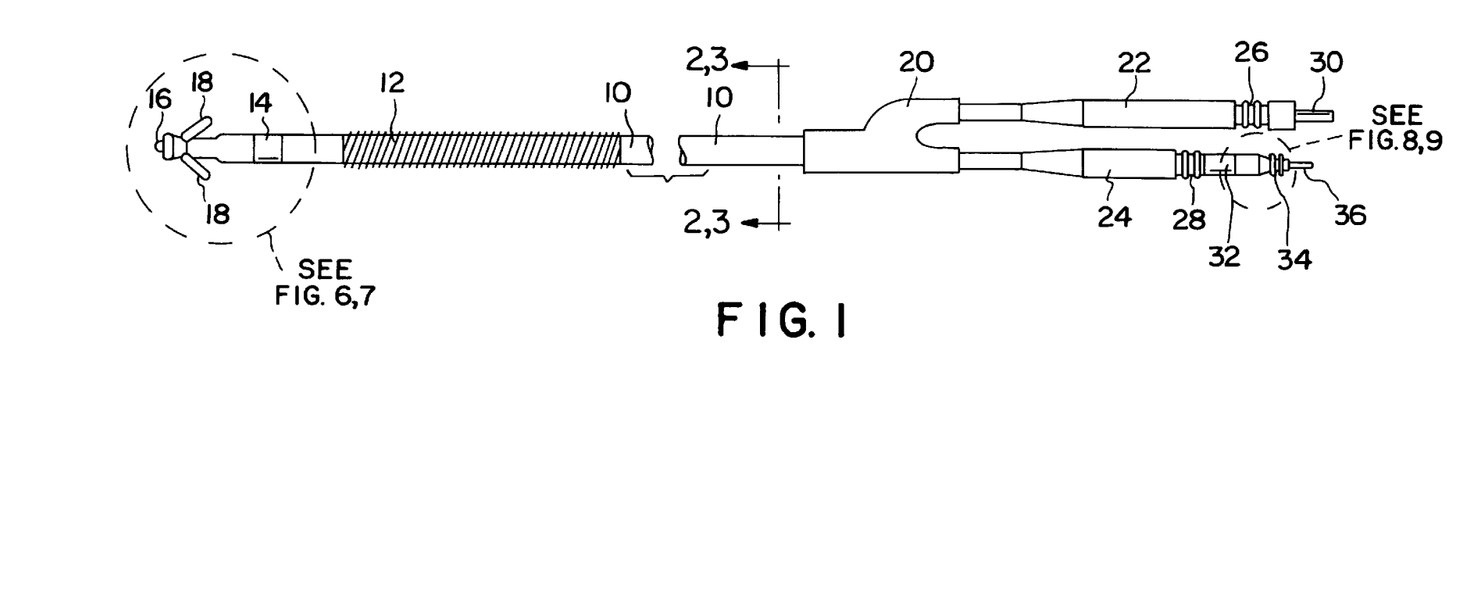
FIG. 1 is a plan view of an implantable lead in which the present invention is practiced.

FIG. 1 is a plan view of a defibrillation lead of a lead in which the present invention is practiced. The present invention, of course, may also be usefully practiced in the context of other types of medical electrical leads, such as cardiac pacing leads, nerve and muscle stimulation leads, and so forth.

The lead of FIG. 1 is provided with an elongated insulative lead body 10, preferably fabricated of silicone rubber, polyurethane or other biocompatible elastomer. At the proximal end of the lead, it carries an elongated defibrillation electrode 12, a ring electrode 14 and a tip electrode 16, each coupled to a conductor located within the lead body 10. Tines 18 are provided in maintaining electrode 16 in contact with the tissue of the right ventricle. Electrodes 16, 14 and 12 may correspond generally to conventionally available pacing and defibrillation electrodes.

The proximal end of the lead carries a connector assembly, beginning with a molded lead bifurcation 20, which splits off two of the conductors within lead body 10 to a bipolar, in-line connector assembly 24, generally corresponding to the IS-1 connector standard for pacing leads. However, other types of connector assemblies may also be adapted to practice the present invention. Connector assembly 24 is provided with a first set of sealing rings 28, a connector ring 32, a second sealing rings 34 and connector pin 36. Connector pin 36 is coupled to the conductor which extends through the lead body 10 to tip electrode 16. Connector ring is coupled to the conductor which extends through the lead body 10 to ring electrode 14. The conductor coupled to defibrillation electrode 12 extends into connector assembly 22, which carries a set of sealing rings 26 and a connector pin 36, coupled to the conductor extending through lead body 10 to defibrillation electrode 12.

In the specific context of the lead illustrated in FIG. 1, the conductor coupling connector pin 36 to electrode 16 takes the form of a monofilar or multifilar coiled conductor to allow passage of a stylet therethrough, while the conductors coupling ring electrode 14 to connector ring 32 and coupling defibrillation electrode 12 to connector pin 30 take the form of bundled, stranded wires, provided with a coating of PTFE. However, the conductors coupling ring electrode 14 and defibrillation electrode 12 may take the form of any of the various conductor types known for use in conjunction with implantable electrical leads. If fewer electrodes are provided on the lead, correspondingly fewer conductors will be included. One or more physiologic sensors may be added to the lead or substituted for one or more of the illustrated electrodes. Also located within lead body 10 is a stranded wire conductor which extends along a length of the coiled conductor and which serves a mechanism for bridging a fracture of the coiled conductor which occurs between the ends of the stranded conductor. In some embodiments, the stranded conductor also couples electrode 16 to connector pin 36, providing both an axial reinforcement and a redundant electrical connection, as described in more detail below. In other embodiments, the electrical interconnection between the coiled and stranded conductors may simply be the contact between the two conductors which occurs as a result of both conductors being located in the same lumen of the lead.

Figure 2:
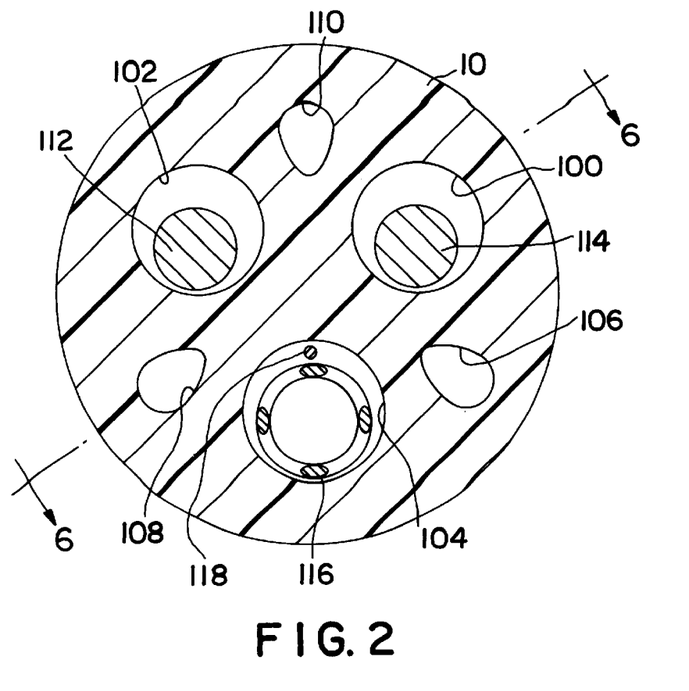
FIG. 2 is cross-sectional view through the lead of FIG. 1, illustrating a first embodiment of the invention.

FIG. 2 illustrates a cross-section through lead body 10, illustrating the interrelation of the conductor lumens 100, 102 and 104 with compression lumens 106, 108 and 110, which are described in more detail in U.S. Pat. No. 5,584,873, issued to Shoberg et al. and incorporated herein by reference in its entirety. In this view it can be seen that lumens 100 and 102 contain conductors 112 and 114 which in the illustrated embodiment may take the form of PTFE coated bundled stranded wires having a generally straight configuration. In particular, conductors 112 and 114 may take the form of a PTFE coated, bundled, stranded 49 filar cable formed of seven strands, each strand formed of seven filars, as described in more detail in U.S. Pat. No. 5,584,873 by Shoberg et al. incorporated herein by reference in its entirety. Lumen 104 contains a conventional multifilar coiled conductor 116 and a small diameter bundled stranded wire conductor 118. Conductor 118 may take the form of a seven filar bundle or cable of MP35N or silver cored MP35N wire, as described in U.S. Pat. No. 5,246,014, issued to Williams et al and also incorporated herein by reference in its entirety, such that conductor 118 corresponds generally to one of the seven strands that make up conductors 112 and 114. In preferred embodiments, conductor 118 may have an outer diameter of about 0.003 inches.

In spite of its small diameter and generally straight configuration, stranded conductor 118 is extremely resistant to fracturing in response to repeated flexure of the lead body and displays a high tensile strength. Thus, should coil conductor 116 fracture, redundant, stranded conductor 118 will remain to provide for connection to the electrode to which coiled conductor 116 is coupled. If the stranded and coiled conductors are uninsulated from one another, they make contact with one another at multiple points along the lead body, so that a break of the coiled conductor occurring between the ends occurring between the ends of the stranded conductor will be bridged. The ends of conductor 118 may also be mechanically coupled to the coiled conductor 116 and thereby serve to maintain the structural integrity of the lead, preventing partial disassembly due to applied tensile forces. If the lead is removed, conductor 118 may thus also serve as a reinforcement, allowing traction force to be applied to the distal end of the lead during extraction. In either case, conductor 118 allows for continued functioning of the lead after fracture of the coiled conductor 116, allowing for replacement of the lead, when convenient, without interruption of the therapeutic function of the pacemaker or stimulator to which the lead is coupled.

In some embodiments of the invention, conductor 118 is uninsulated along its length and thus makes contact with conductor 116 at various points along the length of the lead. In such embodiments, it is to be expected that the conductor 118 will serve as both a redundant conductor, coupling the connector pin 36 to the electrode 16, and as a conductive bridge between the broken ends of the conductor 116, as it will be in contact with the conductor 116 on either side of the break. With this structure, changes in overall impedance between the connector pin and electrode are expected to be relatively small, allowing for essentially undiminished performance of the lead. Alternatively, conductor 118 may be provided with an insulative coating of PTFE or other insulative material. In such embodiments, conductor 118 will serve as a redundant connector, connecting connector pin 32 to electrode 16, and upon fracture of conductor 116, a substantial change in connector pin to electrode impedance will be manifested. In the context of implantable stimulators capable of monitoring changes in lead impedance, this provides the physician and/or the device itself with a mechanism for detecting the fracture in 116. However, within the context of the present invention, the fracture can be detected without the serious consequences which would otherwise be associated with disconnection of the electrode 16 from the connector pin 36. In the context of implantable stimulators having the ability to automatically adjust stimulus pulse amplitude and input amplifier sensitivity, the device may respond to the change in lead impedance by noting the occurrence of a fracture in conductor 116 and may correspondingly alter its programmed parameters in order to restore performance essentially to that preceding the fracture of conductor 116.

Figure 3:
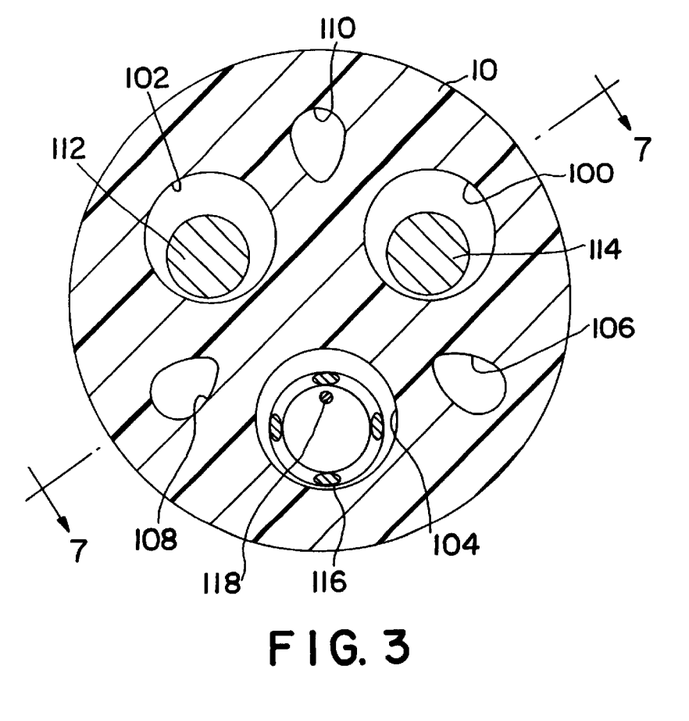
FIG. 3 is cross-sectional view through the lead of FIG. 1, illustrating a second embodiment of the invention.

FIG. 3 is a cross-sectional view through an alternative embodiment of the lead illustrated in FIG. 1, in which all labeled elements correspond to identically labeled elements in FIG. 2. The embodiment illustrated in FIG. 3 differs from that illustrated in FIG. 2 only in that stranded conductor 118 is located within the lumen of conductor 116, rather than external to conductor 116. This embodiment may be particularly advantageous in the context of leads, such as epicardial electrode leads or some nerve and muscle stimulation leads which do not require passage of a stylet through the lumen of coil conductor 116.

Figure 4:
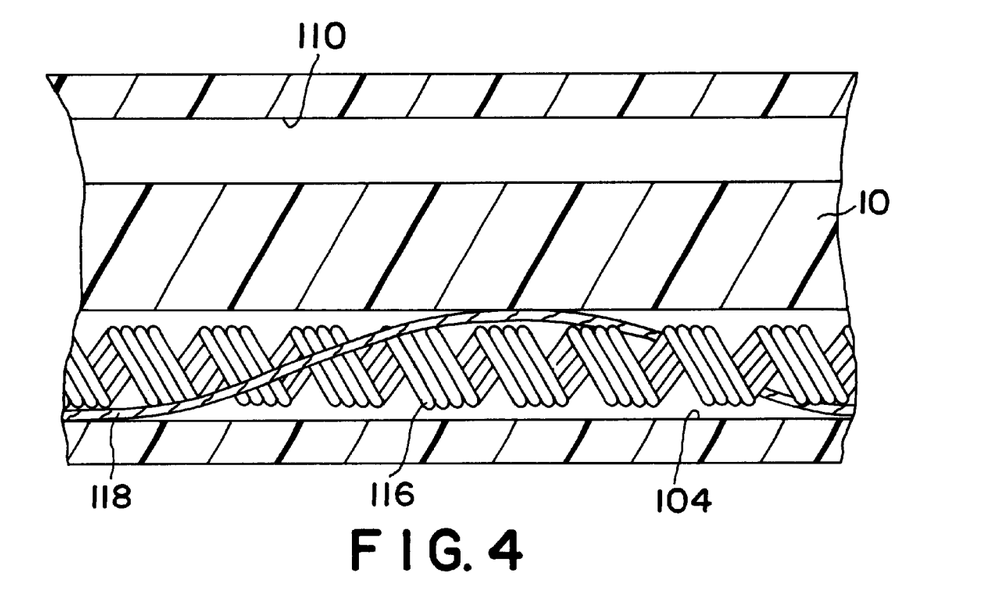
FIG. 4 is a side, cut-away view through the lead of FIG. 1, illustrating the first embodiment of the invention.

FIG. 4 is a side, cutaway view through the lead of FIG. 1, illustrating the first embodiment of the present invention, also illustrated in FIG. 2. In this view, it can be seen that stranded conductor 118 is loosely spiraled around coiled conductor 116 along the length of the lead, facilitating flexure of the lead body and the conductors located therein. If the ends of conductor 118 are mechanically coupled to conductor 116, this structure also allows for a limited amount of axial elongation of the lead body and conductor 116 along the length of conductor 118. All other labeled elements correspond to those illustrated in FIG. 2.

Figure 5:
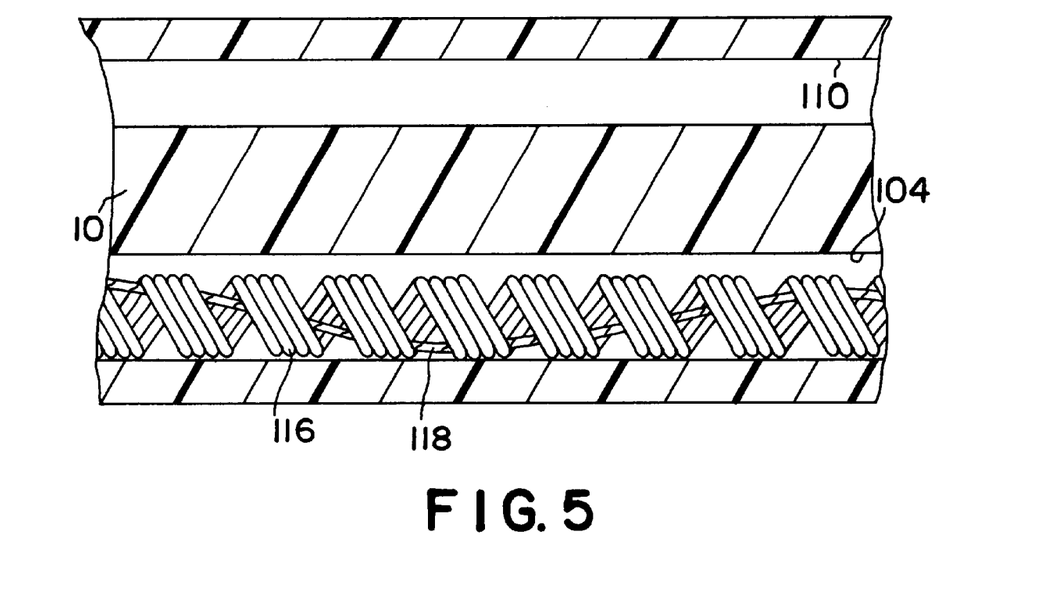
FIG. 5 is a side, cut-away view through the lead of FIG. 1, illustrating the second embodiment of the invention.

FIG. 5 shows a side cutaway view through the second embodiment of the lead of FIG. 1, also illustrated in FIG. 3. In this view, the stranded conductor is shown arranged loosely within the lumen of coiled conductor 116. All other labeled elements correspond to those illustrated in FIG. 2.

In the embodiments illustrated in FIGS. 2, 3, 4 and 5, conductor 118 may be insulated or uninsulated, as discussed above, depending on whether contact between the two conductors along their length is desired. An alternative embodiment in which the stranded conductor is desired to be insulated from the coiled conductor along some portion of its length may employ a separate lumen in the lead body for the stranded conductor, intermediate its points of connection to the coiled conductor. An additional alternative as discussed below may employ a tubular, insulative sheath within or around coiled conductor 116 to insulate it from conductor 118.

Figure 6:
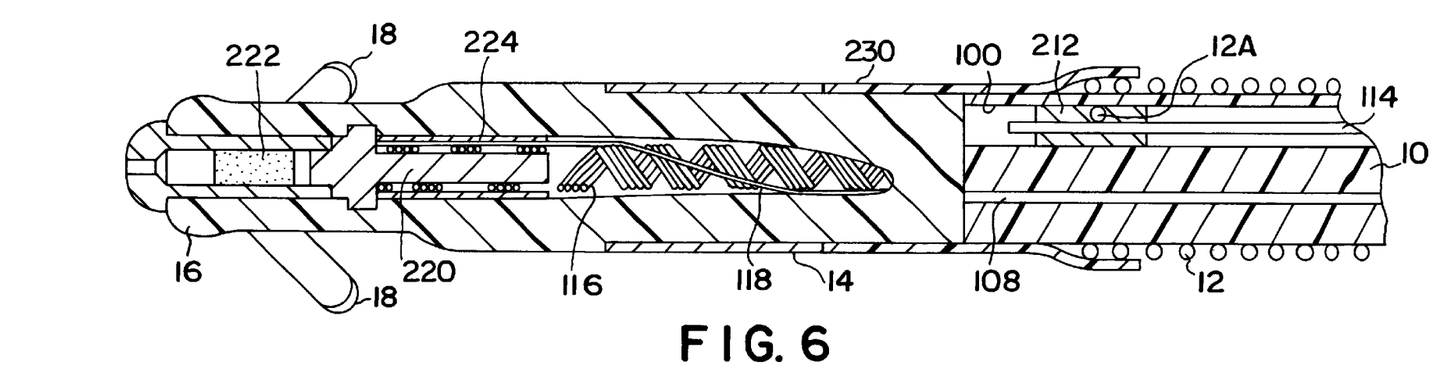
FIG. 6 is a side, cut-away view through the distal portion of the lead of FIG. 1, illustrating the first embodiment of the invention.

FIGS. 6 et seq. show basic mechanisms which may optionally be employed to mechanically interconnect the stranded conductor 118, the coiled conductor 116, electrode 16 and connector pin 36. These illustrated interconnection mechanisms are intended to be exemplary, and may of course, be employed in conjunction with other components of implantable leads, including other types of electrical connectors such as connector rings, corresponding to connector ring 32 and to interconnect these conductors with other types of electrodes and to interconnect these components with other lead components such as physiologic sensors such as pressure sensors, oxygen sensors, temperature sensors and the like.

FIG. 6 is a sectional view through the distal portion of the lead illustrated in FIG. 1. In this view, the interconnection of conductor 116, conductor 118 and electrode 16 is visible. Extending distally from the defibrillation electrode 12, the lead takes the form of a molded piece part 228, which carries ring electrode 14, which is in turn coupled to stranded conductor 112 (not visible in this view). Electrode 16 as illustrated is a steroid-eluting electrode, provided with a monolithic controlled release device 222 located within a chamber within the electrode. Electrode 16 is coupled to a coiled conductor 116 and 118 by means of an external crimping sleeve 224, which compresses conductor 118 against conductor 116 and compresses conductor 116 against the proximal portion 220 of electrode 16. Other types of tip electrodes, including screw-in electrodes may of course be substituted for electrode 16. Similarly, other mechanisms may be employed to interconnect conductors 118 and 116 and electrode 16, including welding, swaging, crimping and combinations thereof, including mechanisms as disclosed in commonly assigned, copending U.S. patent application Ser. No. 08/657,577 by Boser et al, filed Jun. 7, 1996 and U.S. patent application Ser. No. 08/439,332 by Swoyer et al., filed May 11, 1995, both incorporated herein by reference in their entireties.

Conductor 114 passes through an internal lumen 100 within lead body 10, and has its insulation removed in areas in which it passes through the cross-bore crimp sleeve 212. The distal turn of electrode coil 12 can be seen at 12A as it passes through the perpendicular cross-bore through sleeve 212. The sleeve 212 is crimped to the conductor 114 and a portion of the distal turn of electrode coil 12 is inserted through the cross bore and the entry and exit points of the coil are laser welded to the sleeve. External polymeric sleeve 230 is slid over the distal ends of conductor coil 12, and the areas between the sleeve 230 lead body 10 is backfilled by means of medical adhesive or other polymeric material. The electrode coil 12 may be secured to the outer circumference of the lead body 10 by means of a backfilling process as described in U.S. Pat. No. 4,934,049, incorporated herein by reference in its entirety.

Figure 7:
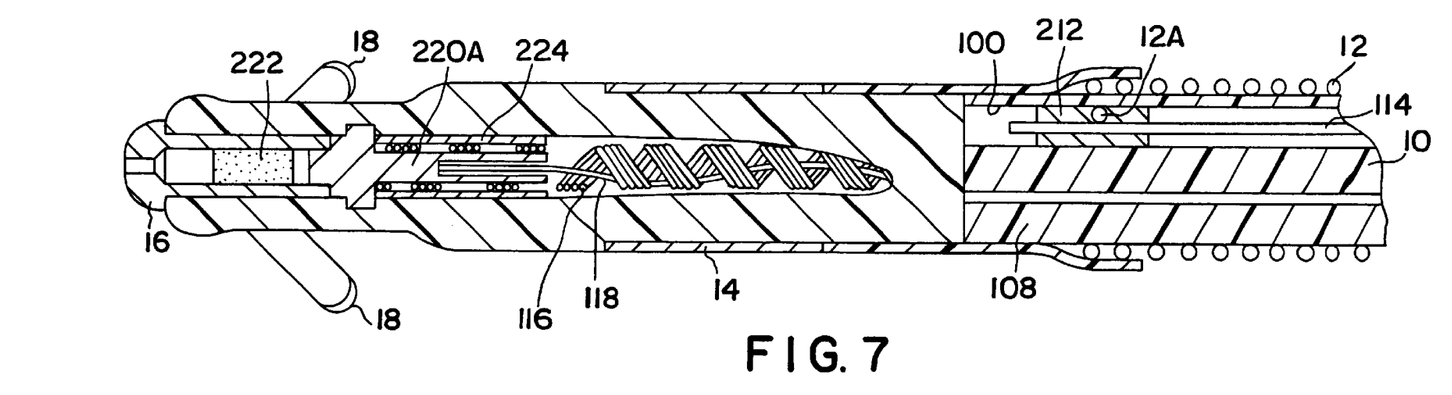
FIG. 7 is a side, cut-away view through the distal portion of the lead of FIG. 1, illustrating the second embodiment of the invention.

FIG. 7 illustrates the distal portion of the lead in the second embodiment of the invention in which the stranded conductor 118 is located internal to coil conductor 116. All illustrated elements correspond to identically numbered elements in FIG. 6, with the exception that a bore is provided in the proximal section 220A of electrode 16, and stranded conductor 118 is crimped therein.

While FIGS. 6 and 7 show the inter-connection of the stranded and coiled conductors at the tip electrode 16, these conductors may instead be connected at a point proximal to the tip electrode, for example by use of a cross-bore crimp sleeve similar to sleeve 212, or by means of other types of welded, swaged or crimped connections as discussed above.

Figure 8:
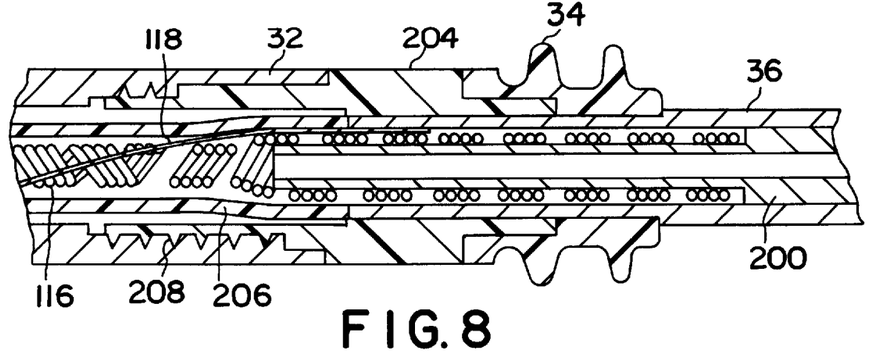
FIG. 8 is a side, cut-away view through the connector assembly of the lead of FIG. 1, illustrating the first embodiment of the invention.

FIG. 8 is sectional view through the bipolar connector assembly 24 of the lead illustrated in FIG. 1, illustrating the first embodiment of the invention. In this view, the proximal end of connector pin 36 is visible in cross-section, and connector ring 32 is visible in cross-section. Connector pin 36 is coupled to coiled conductor 116 by means of a swaging core 200, which compresses conductor coil 116 and stranded conductor 118 between the interior lumen of connector pin 36 and the outer surface of swaging core 200, in a conventional fashion. An insulative sleeve 206 surrounds conductors 116 and 118, and extends distally, back through the connector assembly into molded sealing ring sleeve 28 (FIG. 1).

Surrounding connector pin 36 is a molded sealing ring sleeve 34, which may be fabricated of silicone rubber, which in turn is mounted to a spacer 204 which is typically fabricated of a harder plastic, such as polyurethane. Spacer 204 is molded in situ between connector pin 36 and ring electrode 32, and is maintained in mechanical interconnection with electrode 32 by means of internal threading 208, as described in U.S. Pat. No. 4,572,605, issued to Hess, et al., incorporated herein by reference in its entirety.

Figure 9:
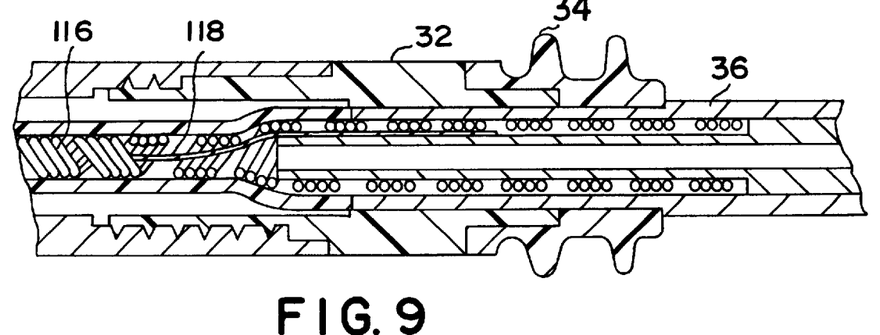
FIG. 9 is a side, cut-away view through the connector assembly of the lead of FIG. 1, illustrating the second embodiment of the invention.

FIG. 9 is a sectional view through the bipolar connector assembly 24 of the lead illustrated in FIG. 1, illustrating the second embodiment of the invention. All illustrated elements correspond to identically numbered elements in FIG. 8, with the exception that the stranded conductor 118 is located internal to coil conductor 116.

As in the case of FIGS. 6 and 7 above, other mechanisms may be employed to interconnect conductors 118 and 116 and connector pin 36, including welding, swaging, crimping and combinations thereof, as described above. Additionally, these conductors may instead be connected at a point distal to the connector pin, for example by use of a cross-bore crimp sleeve similar to sleeve 212, or by means of other types of welded, swaged or crimped connections as discussed above.

If it is not desired to mechanically interconnect on or both ends of the stranded conductor 118 to the coiled conductor 116, the internal structure of the leads may correspond to those illustrated in FIGS. 6, 7, 8 or 9 above, with the exception the stranded conductor 118 is simply not crimped, swaged or otherwise coupled to the connector pin, electrode or coiled conductor 118. In such embodiments, the stranded conductor may extend the entire length of the coiled conductor or may extend over only a portion of the length of the coiled conductor. While the FIGS. 6, 7, 8 and 9 illustrate the coil and stranded conductor pair coupled to the connector pin and tip electrode, it should also be understood that the invention may also be usefully practiced in leads in which these conductors are coupled to other connector elements, other electrodes and/or physiologic sensors located on the lead body. The interconnection methods of FIGS. 6, 7, 8 and 9 may also be used to connect the stranded conductor 118 to the coiled conductor 116 and to such other lead components.

Figure 10:
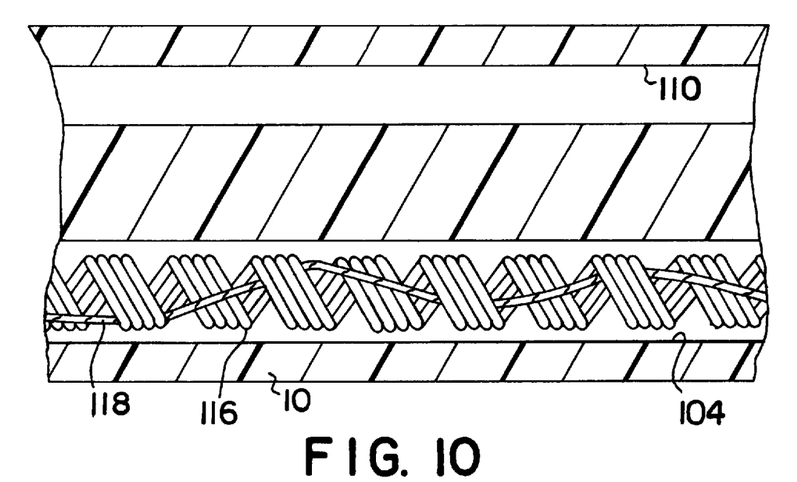
FIG. 10 is a side, cut-away view through the lead of FIG. 1, illustrating a third embodiment of the invention.

FIG. 10 illustrates a third embodiment of the invention All numbered components correspond to identically numbered components in the Figures above. In this embodiment, an uninsulated stranded conductor 118 repeatedly enters and exits the internal lumen of the coiled conductor 116, by passing between the coils. This embodiment, while more difficult to assemble, provides for in increase in the number of contact points between the stranded and coiled conductors, which may be beneficial in the case of coil fractures as it will in many case shorten the distance which the stranded conductor must bridge as compared to the first and second embodiments and may provide for more consistent contacts between the stranded and coiled conductors.

Figure 11:
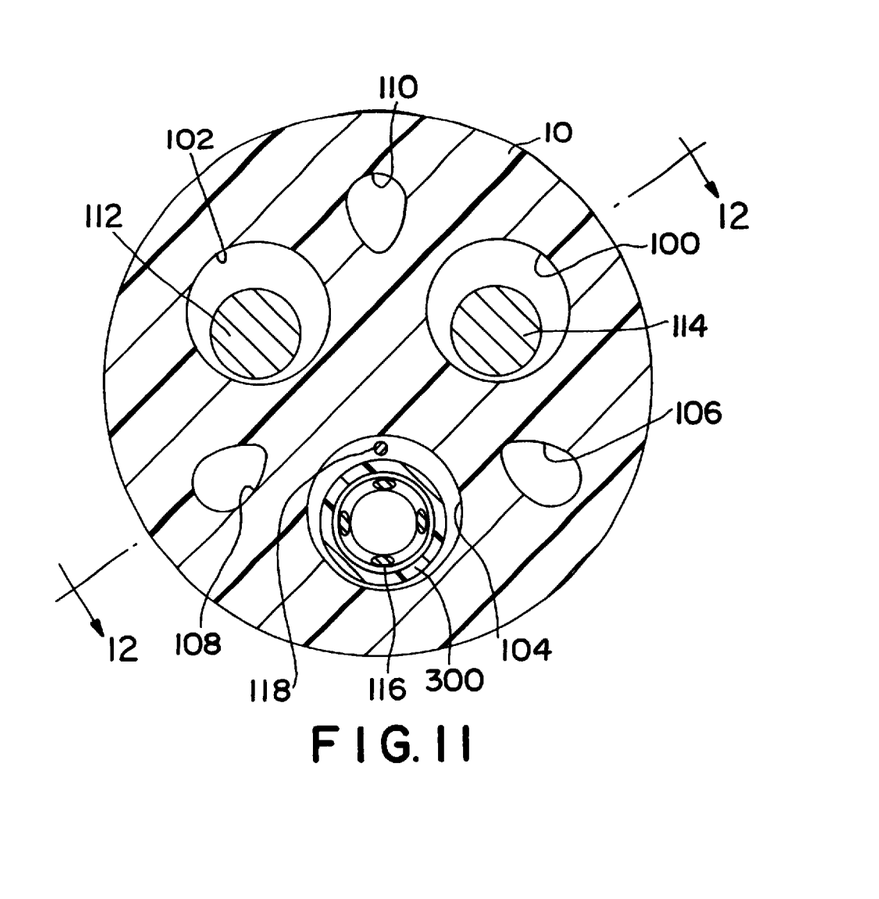
FIG. 11 is cross-sectional view through the lead of FIG. 1, illustrating a fourth embodiment of the invention.

FIG. 11 illustrates a cross section through a fourth embodiment of the invention. All numbered components correspond to identically numbered components in the Figures above. In this embodiment the stranded conductor 118 is located outside of coiled conductor 116 and is insulated from conductor 116 over at least a portion of its length by means of an insulative tube 300, located exterior to conductor 116. Tube 300 may be formed of PTFE or other insulative biocompatible plastic, and may extend over all or some of the length of coiled conductor 116. In this embodiment, it is desirable that the ends of stranded conductor 118 are mechanically coupled to the coiled conductor 116 on either side of the tube 300.

Figure 12:
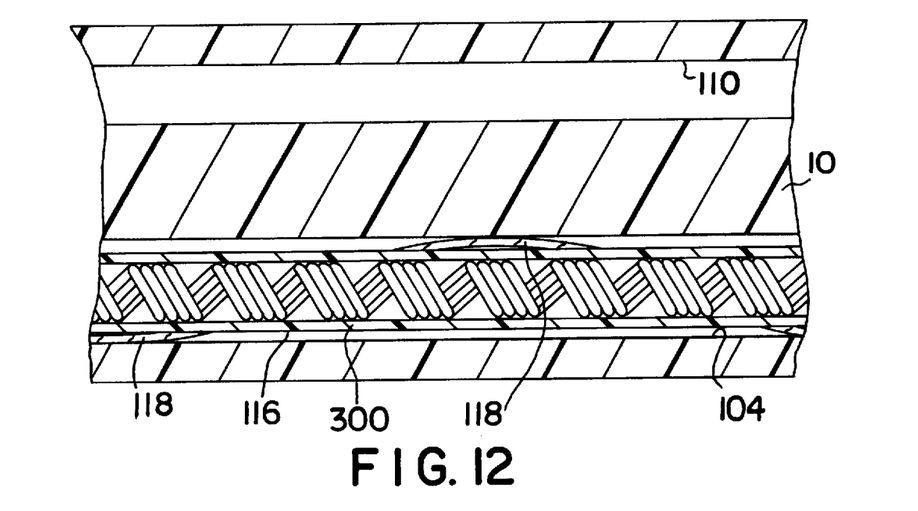
FIG. 12 is a side, cut-away view through the lead of FIG. 1, illustrating the fourth embodiment of the invention.

FIG. 12 illustrates a side, cut-away view through the fourth embodiment of the invention as illustrated in FIG. 11. All numbered components correspond to identically numbered components in the Figures above.

Figure 13:
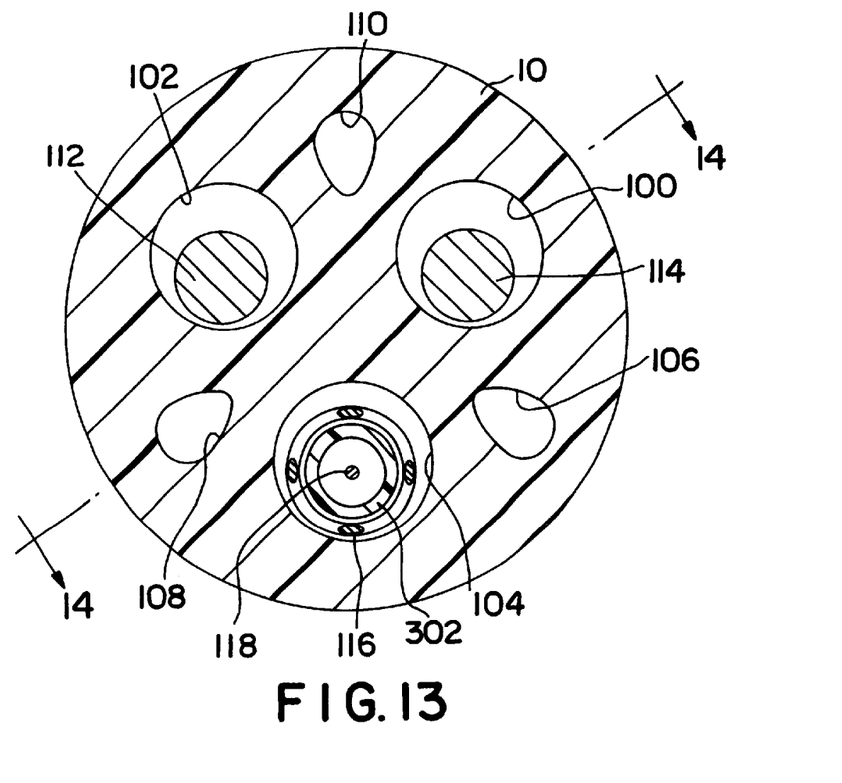
FIG. 13 is cross-sectional view through the lead of FIG. 1, illustrating a fifth embodiment of the invention.

FIG. 13 illustrates a cross section through a fifth embodiment of the invention All numbered components correspond to identically numbered components in the Figures above. In this embodiment the stranded conductor 118 is located inside of coiled conductor 116 and is insulated from conductor 116 over at least a portion of its length by means of an insulative tube 302, located interior to conductor 116. Tube 302 may be formed of PTFE or other insulative biocompatible plastic, and may extend along all or some of the length of coiled conductor 116. In this embodiment, it is desirable that the ends of stranded conductor 118 are mechanically coupled to the coiled conductor 116 on either side of the tube 302.

Figure 14:
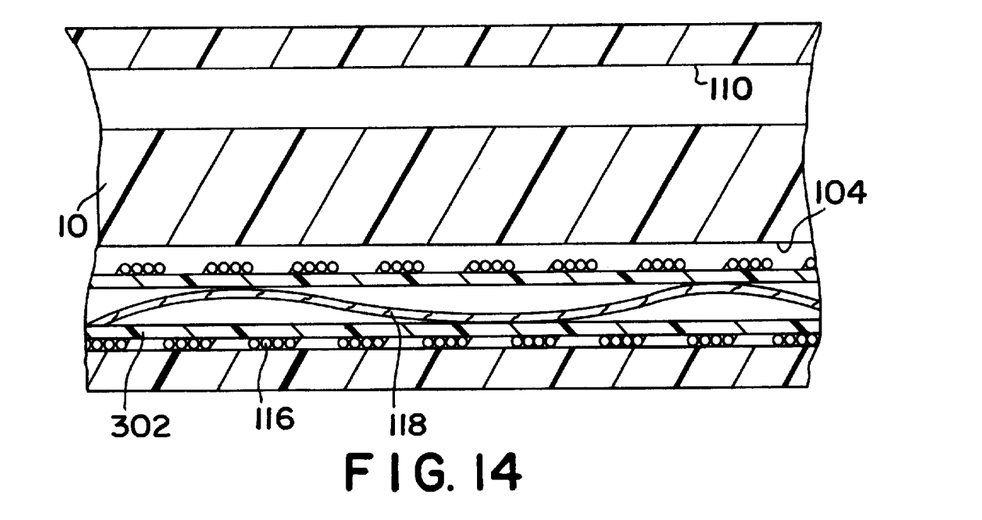
FIG. 14 is a side, cut-away view through the lead of FIG. 1, illustrating the fifth embodiment of the invention.

FIG. 14 illustrates a side, cut-away view through the fifth embodiment of the invention as illustrated in FIG. 13. All numbered components correspond to identically numbered components in the Figures above.

Figure 15:
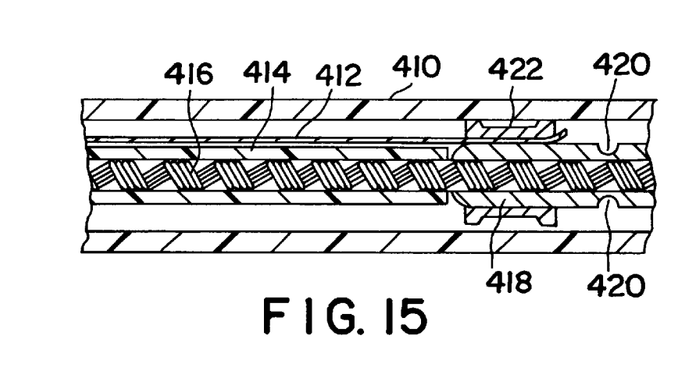
FIG. 15 is a side, cut-away view through the a lead according to the present invention, illustrating an alternative mechanism for interconnecting a coiled conductor with a stranded conductor.

FIG. 15 illustrates an alternative mechanism for interconnecting a stranded conductor 412 with a coiled conductor 416, both located within an internal lumen of lead body 410. Conductive crimp sleeve 418 is crimped to coiled conductor 416 by crimps 420. Optionally, a cylindrical crimping core (not illustrated) may be inserted into the lumen of coiled conductor 416, prior to crimping. Stranded conductor 412 is coupled to the crimp sleeve 418 by means of conductive sleeve 422, by the following methods. Stranded conductor 412 may be threaded through sleeve 422, which is then pushed onto crimping core 418, pulling stranded conductor 412 along and compressing it between crimp sleeve 418 and sleeve 422. In conjunction with this method, the interior of sleeve 422 may be provided with threads or other internal texturing to frictionally engage stranded conductor 412. Alternatively, stranded conductor 412 may arranged alongside crimp core 418 and sleeve 422, may then be pushed onto crimp core 418, compressing conductor 412 between crimp sleeve 418 and sleeve 422. In conjunction with this method, the exterior of crimp of sleeve 418 may be provided with threads or other external texturing to frictionally engage stranded conductor 412. As yet another alternative, sleeve 422 may simply be crimped around stranded conductor 412 and crimping sleeve 418. Crimp sleeve 418 may take the form of a portion of a connector pin or ring on the proximal end of the lead body or a portion of an electrode or other sensor on the distal portion of the lead body, or may simply be a cylindrical sleeve, employed to couple the stranded and coiled conductors at some point along the lead body. Plastic Sleeve 414 insulated stranded conductor 412 from coiled conductor 416 over a portion of their lengths.

Figure 16:
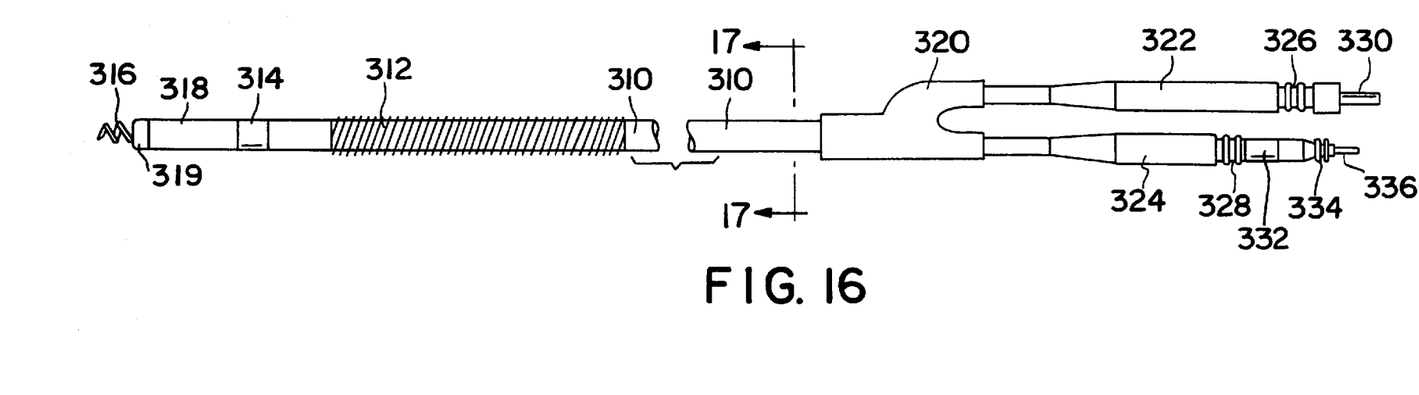
FIG. 16 is a plan view of a lead having a rotatable fixation helix, embodying the present invention.

FIG. 16 is a plan view of a defibrillation lead in which the present invention is practiced, employing a tip electrode taking the form of a rotatable fixation helix 316. The lead of FIG. 16 is provided with an elongated insulative lead body 310, preferably fabricated of silicone rubber, polyurethane or other biocompatible elastomer. At the distal end of the lead, it carries an elongated defibrillation electrode 312, a ring electrode 314 and a rotatable helical tip electrode 316, rotatably and advancably mounted in insulative electrode head 318. Each electrode is coupled to a conductor located within the lead body 310. Electrodes 314 and 312 may correspond generally to conventionally available pacing and defibrillation electrodes. A cap member 319 is located at the distal end of electrode head 318 and serves to retain a monolithic controlled release device as discussed below.

The proximal end of the lead carries a connector assembly, beginning with a molded lead bifurcation 320, which splits off two of the conductors within lead body 310 to a bipolar, in-line connector assembly 324, generally corresponding to the IS-1 connector standard for pacing leads. However, other types of connector assemblies may also be adapted to practice the present invention. Connector assembly 324 is provided with a first set of sealing rings 328, a connector ring 332, a second sealing rings 334 and connector pin 336. Connector pin 336 is rotatably mounted and is coupled to a rotatably mounted conductor which extends through the lead body 310 to helical electrode 316. Connector ring 332 is coupled to a conductor which extends through the lead body 310 to ring electrode 314. A conductor coupled to defibrillation electrode 312 extends into connector assembly 322, which carries a set of sealing rings 326 and is coupled to connector pin 336.

In the specific context of the lead illustrated in FIG. 16, the conductor coupling connector pin 336 to electrode 316 takes the form of a monofilar or multifilar coiled conductor to allow passage of a stylet therethrough, while the conductors coupling ring electrode 314 to connector ring 332 and coupling defibrillation electrode 312 to connector pin 330 take the form of bundled, stranded wires, provided with a coating of PTFE. However, the conductors coupling ring electrode 314 and defibrillation electrode 312 may take the form of any of the various conductor types known for use in conjunction with implantable electrical leads. If fewer electrodes are provided on the lead, correspondingly fewer conductors will be included. One or more physiologic sensors may be added to the lead or substituted for one or more of the illustrated electrodes. Also located within lead body 310 is a stranded wire conductor which extends along a length of the coiled conductor and which serves a mechanism for bridging a fracture of the coiled conductor which occurs between the ends of the stranded conductor, as discussed above.

Figure 17:
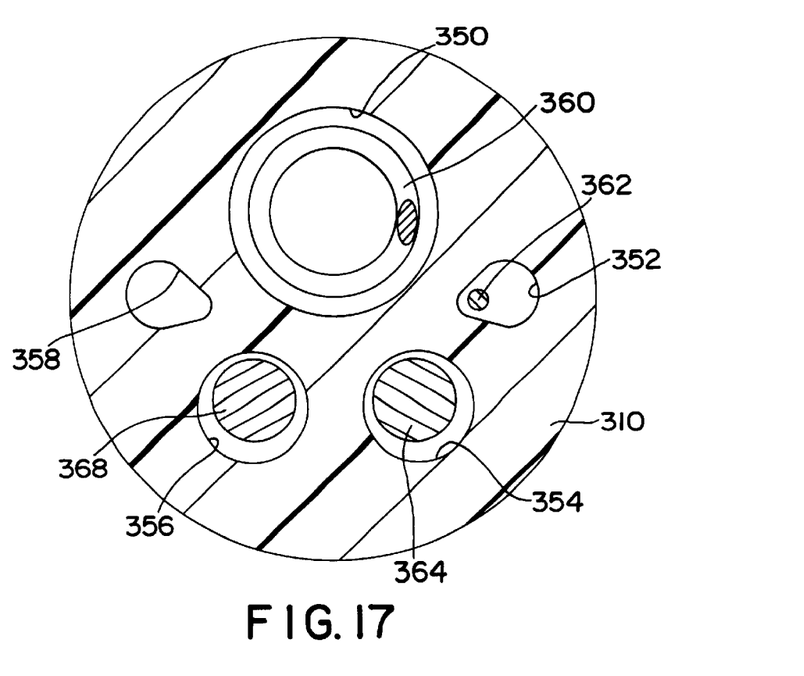
FIG. 17 is a cross-sectional view through the lead of FIG. 16.

FIG. 17 illustrates a cross section through the lead illustrated in FIG. 16. The lead body is provided with five lumens, including three circular lumens 350, 354 and 356 and two teardrop-shaped compression lumens 352 and 358. Coiled conductor 360 is coupled to helical electrode 316 (FIG. 16) and connector pin 336 (FIG. 16). On rotation of connector pin 336, conductor 360 transmits torque to rotate electrode 316, advancing it out the distal end of electrode head 318 (FIG. 16) and screwing it into heart tissue. Conductors 364 and 368 as illustrated are stranded or cabled conductors corresponding to conductors 112 and 114 (FIG. 2) and couple connector pin 330 to defibrillation electrode 312 and connector ring 332 to electrode 314, respectively. Stranded conductor 362 is coupled to coiled conductor 360 adjacent the proximal and distal ends of the lead, providing a redundant connector and tensile reinforcement in the same fashion as conductor 118 (FIG. 2) discussed above. The wall of lead body 310 separating lumens 350 and 352 insulates conductor 362 from conductor 360 between the points at which they are electrically coupled. Electrical interconnection of conductors 360 and 362 is by means of rotating electrical couplings as described in conjunction with FIGS. 18 and 19 below, which allow rotation of coil conductor 360 relative to stranded conductor 362.

Figure 18:
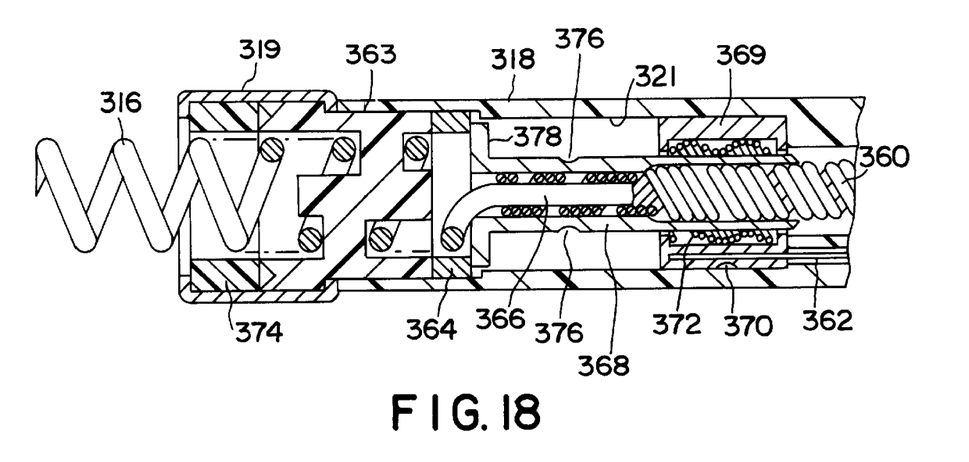
FIG. 18 is a side, cut-away view through the distal portion of the lead of FIG. 16.

FIG. 18 is a side cut-away view through the distal portion of electrode head 318 of the lead of FIG. 16. Electrode head 318 is fabricated of a rigid, biocompatible plastic such as a polyurethane, and is provided with an internal longitudinal lumen 321. Cap 319 retains a toroidal monolithic controlled release device 374, which serves to elute an anti-inflammatory steroid such as sodium dexamethasone phosphate, as described in U.S. Pat. No. 4,972,848, issued to DiDomrmico and incorporated herein by reference in its entirety. Guide 363 engages helical electrode 316 such that rotation of the electrode serves to advance it out the distal end of electrode head 318 or withdraw it into lumen 321. Coiled conductor 360 is mechanically and electrically coupled to the proximal end of electrode 316 by conductive crimp sleeve 368, compressed by crimps 376. Crimp sleeve 368 is provided with a circumferential shoulder 378 which serves to limit distal movement of helix 316 by contact with radio-opaque marker ring 364 and which serves to limit proximal movement of helix 316 by contact with conductive ferrule 369.

Electrical interconnection of stranded conductor 362 and coiled conductor 360 is accomplished by ferrule 369 which is crimped to stranded conductor 362 by crimp 370 and is provided with contact means 372 for coupling to conductive crimp sleeve 368. As illustrated the contact means 372 is a conductive spring with individual turns offset from one another to springingly contact both ferrule 369 and crimp sleeve 368 while allowing rotation and longitudinal movement of crimp sleeve 368, in a manner analogous to that illustrated in U.S. Pat. No. 4,557,643, incorporated herein by reference in its entirety. Alternatively, coupling means in the form of other types of spring contacts, fine wire brushes or other known mechanisms for rotatable electrical couplings may be substituted.

Figure 19:
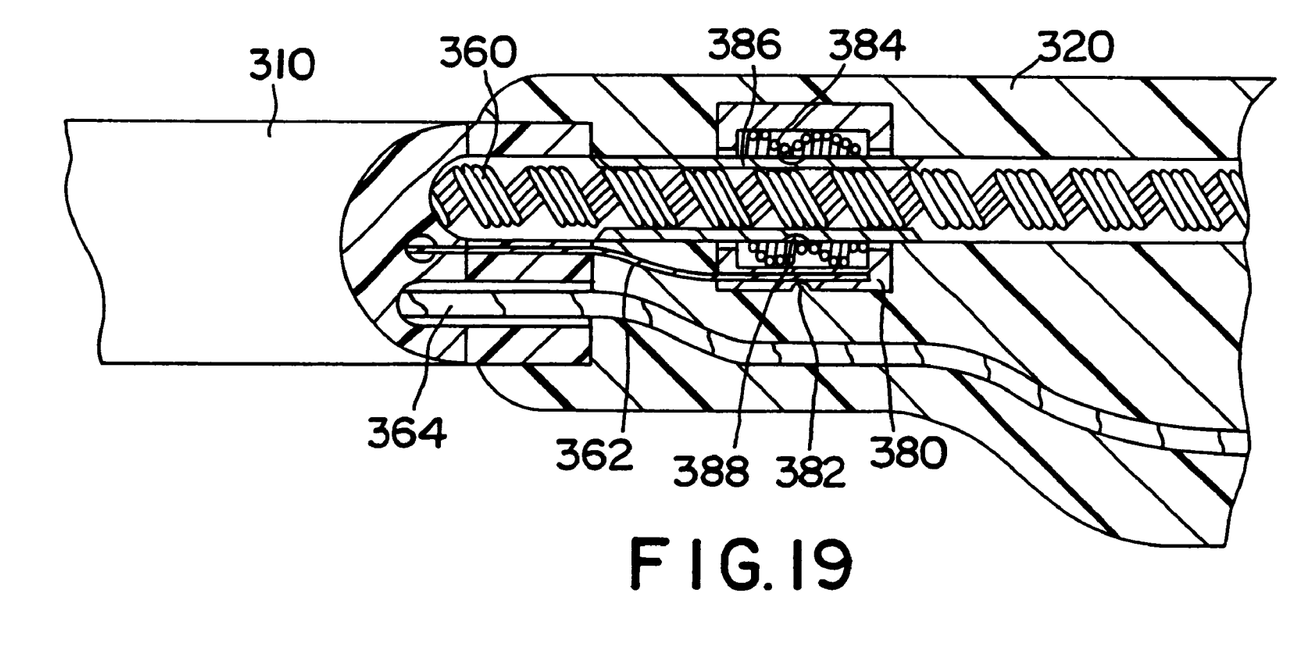
FIG. 19 is a side, cut-away view through the proximal portion of the lead of FIG. 16.

FIG. 19 shows a side, cut-away view through the lead of FIG. 16 in the vicinity of bifurcation 320. In this view, coiled conductor 360 and stranded conductors 362 and 364 are visible, exiting from lead body 310 and entering into molded bifurcation 320. Interconnection of stranded conductor 362 and coiled conductor 360 is accomplished by ferrule 380 coupled to conductor 362 by crimp 382, crimp sleeve 386 coupled to coiled conductor 360 by crimps 388 and conductive spring 384. These components function in the same way as their counterparts illustrated in FIG. 18 to couple the conductors while allowing rotational movement of coiled conductor 360. As in the case of FIG. 18, the known mechanisms for making a rotating electrical connection may be substituted. While the rotatable coiled conductor in this embodiment is coupled to a helical electrode, it may alternatively be coupled to any other electrode which is deployed or manipulated by applied torque and may also be employed with any other mechanism requiring both applied torque and an electrical connection.

While the embodiments described above are shown as alternatives it should be understood that they also may be combined, with the location and insulation of the stranded conductor relative to the coiled conductor varying along the length of the lead body. In addition, while the embodiments above all take the form of multiple lumen leads fabricated using multi-lumen tubing, it should be understood that the invention may also usefully be practiced in embodiments having only a single lumen and in embodiments in which multiple lumens are provided by means of single lumen tubes located within larger diameter single lumen tubes. As such, the disclosure above should be taken as exemplary, rather than limiting with regard to the scope of the claims which follow. In conjunction with the above disclosure, we claim:

What is claimed is:

1. An implanted medical lead comprising an elongated lead body having an elongated lumen therein;
    an elongated coiled conductor defining an internal lumen and mounted within the lumen of the lead body;
    a stranded conductor, extending along the length of the lead body and coupled electrically to the coiled conductor at a first location and a second location distal to and spaced from the first location, said stranded conductor located outside of said internal lumen of said coiled conductor for a distance extending along said lead body.

2. A lead according to claim 1 wherein said lead is provided with an electrical connector located at a proximal end of the lead body and in which the coiled conductor is connected to the connector.

3. A lead according to claim 2 in which the stranded conductor and the coiled conductor are electrically and mechanically coupled to the connector.

4. A lead according to claim 1 or claim 2 wherein said stranded conductor and said coiled conductor are both located within said lumen of said lead body.

5. A lead according to claim 1 provided with an electrode located on said lead body and in which the coiled conductor is coupled to the electrode.

6. A lead according to claim 5 wherein the coiled conductor and the stranded conductor are both electrically and mechanically coupled to the electrode.

7. A lead according to claim 1 provided with an electrical component located on said lead body, wherein said coiled conductor is coupled to said electrical component.

8. A lead according to claim 7 wherein said coiled conductor and said stranded conductor are electrically and mechanically coupled to said electrical component.

9. A lead according to claim 7 wherein said electrical component is an electrode.

10. A lead according to claim 1 wherein said stranded conductor comprises a seven stranded conductor.

11. A lead according to claim 10 wherein said stranded conductor is made of MP35N alloy.

12. A lead according to either claim 10 or 11 wherein said stranded conductor has an outer diameter of about 0.003 inches.

13. A lead according to claim 1 in which the stranded conductor and the coiled conductor are electrically and mechanically coupled to one another.

14. A lead according to claim 13 in which the stranded conductor and the coiled conductor are electrically and mechanically coupled to one another at said first and second locations.

15. An implantable medical lead comprising an elongated lead body having an elongated lumen therein;

an elongated coiled conductor defining an internal lumen and mounted within the lumen of the lead body;

a bundled stranded conductor having a generally sraight configuration, extending along the length of the lead body and coupled electrically to the coiled conductor at a first location and a second location distal to and spaced from the first location, said bundled, stranded conductor located outside of said internal lumen of said coiled conductor for a distance extending along said lead body.

16. A lead according to claim 15 wherein said lead is provided with an electrical connector located at a proximal end of the lead body and in which the coiled conductor is connected to the connector.

17. A lead according to claim 16 in which the stranded conductor and the coiled conductor are electrically and mechanically coupled to the connector.

18. A lead according to claim 15 provided with an electrode located on said lead body and in which the coiled conductor is coupled to the electrode.

19. A lead according to claim 18 wherein the coiled conductor and the stranded conductor are both electrically and mechanically coupled to the electrode.

20. A lead according to claim 15 provided with an electrical component located on said lead body, wherein said coiled conductor is coupled to said electrical component.

21. A lead according to claim 20 wherein said coiled conductor and said stranded conductor are electrically and mechanically coupled to said electrical component.

22. A lead according to claim 21 wherein said electrical component is an electrode.

23. A lead according to claim 15 or claim 16 or claim 18 or claim 20 wherein said stranded conductor and said coiled conductor are both located within said lumen of said lead body.

24. A lead according to claim 23 wherein said stranded conductor comprises a seven stranded conductor.

25. A lead according to claim 24 wherein said stranded conductor is made of MP35N alloy.

26. A lead according to claim 23 wherein said stranded conductor has an outer diameter of about 0.003 inches.

27. A lead according to claim 23 wherein said stranded conductor is a cabled conductor.

28. A lead according to claim 23 wherein said coiled conductor is a multi-filar coil conductor.

29. A lead according to claim 28 wherein said stranded conductor is a cabled conductor.

30. A lead according to claim 15 or claim 16 or claim 18 or claim 20 wherein said stranded conductor is a cabled conductor.

31. A lead according to claim 30 wherein said coiled conductor is a multi-filar coil conductor.

32. A lead according to claim 15 or claim 16 or claim 18 or claim 20 wherein said coiled conductor is a multi-filar coil conductor.

33. A lead according to claim 32 wherein said stranded conductor is a cabled conductor.

34. A lead according to claim 15 in which the stranded conductor and the coiled conductor are electrically and mechanically coupled to one another.

35. A lead according to claim 34 in which the stranded conductor and the coiled conductor are electrically and mechanically coupled to one another at said first and second locations.

* * * * *